United States Patent [19]

Müller et al.

[11] Patent Number: 4,547,483

[45] Date of Patent: Oct. 15, 1985

[54] CATALYSTS FOR FLUORINATION AND/OR DISMUTATION REACTIONS ON HALOGENATED HYDROCARBONS, AND A PROCESS FOR THEIR PREPARATION

[75] Inventors: Thomas Müller, Bad Homburg; Günter Siegemund, Hofheim am Taunus, both of Fed. Rep. of Germany

[73] Assignee: Hoechst Aktiengesellschaft, Fed. Rep. of Germany

[21] Appl. No.: 624,936

[22] Filed: Jun. 27, 1984

[30] Foreign Application Priority Data

Jun. 29, 1983 [DE] Fed. Rep. of Germany ....... 3323374

[51] Int. Cl.[4] .................... B01J 27/12; B01J 21/18; C07C 17/20; C07C 19/08
[52] U.S. Cl. .................... 502/226; 502/181; 502/228; 570/166; 570/168; 570/169
[58] Field of Search .................... 502/226, 228, 181; 570/159, 160, 168, 169, 166

[56] References Cited

U.S. PATENT DOCUMENTS 3,043,889  7/1962  Smith et al. .................... 502/228
3,992,325  11/1976  Knaak .................... 570/168

FOREIGN PATENT DOCUMENTS 49-43922  11/1974  Japan .................... 570/169

Primary Examiner—P. E. Konopka
Attorney, Agent, or Firm—Connolly and Hutz

[57] ABSTRACT

A process is specified for preparing a chromium- and magnesium-containing catalyst for fluorination reactions by precipitating chromium(III) hydroxide. In this process, 1 mole of a water-soluble chromium(III) salt is reacted with at least 1.5 moles of magnesium hydroxide or magnesium oxide in the presence of water, and the reaction mixture—if necessary by evaporation—is converted into a paste which contains chromium(III) hydroxide and a magnesium salt. The paste is dried and treated with hydrogen fluoride at temperatures of 20° to 500° C.

6 Claims, No Drawings

CATALYSTS FOR FLUORINATION AND/OR DISMUTATION REACTIONS ON HALOGENATED HYDROCARBONS, AND A PROCESS FOR THEIR PREPARATION

The invention relates to new, active and selective chromium-containing catalysts and a process for their preparation. The catalysts can be used in the fluorination of halogenated hydrocarbons, in particular aliphatic chlorohydrocarbons, with hydrogen fluoride in the gas phase or for the dismutation of fluorine-containing hydrocarbons.

There are a number of prior art methods of preparing chromium-containing catalysts. For instance, it is possible to obtain an active catalyst by subjecting a hydrated oxide of trivalent chromium to a thermal treatment and/or a fluorination with hydrogen fluoride. Hydrated oxides of trivalent chromium [$Cr_2O_3$ X $H_2O$] can also be thought of as being the various hydrated forms of chromium(III) hydroxide (see Friche-Hütting, "Hydroxide und Oxidhydrate [Hydroxides and hydrated oxides]", Leipzig, 1937, pages 252 to 268).

Hydrated chromium oxides can be obtained by reacting a hexavalent chromium compound with a reducing agent such as alcohol (U.S. Pat. No. 3,258,500) and activating the precipitated hydroxide by heating it to about 500° C. The catalyst which is obtained is in the main composed of $Cr_2O_3$.

Hydrated chromium oxides which are obtained by reducing hexavalent chromium compounds in a boric acid fusion, for example Guignet's Green, are suitable starting materials for fluorination catalysts provided they have been (expensively) washed to remove boron-containing admixtures.

It is a disadvantage of the preparation methods outlined that chromium(VI) compounds are used, since these compounds are carcinogenic and toxic and therefore necessitate much expenditure on industrial safety measures.

It is also possible to precipitate hydrated chromium oxide from an aqueous solution of a trivalent chromium compound with an alkaline precipitant such as ammonium hydroxide and by drying to obtain a chromium oxide catalyst (German Offenlegungsschrift No. 1,443,382). Hydrated chromium oxide in the γ-form can also be brought into a catalytically active form by thermal treatment (U.S. Pat. No. 3,426,009) and/or fluorination with hydrogen fluoride (German Offenlegungsschrift No. 1,252,182).

This has the disadvantage that precipitated hydrated chromium oxide has to be washed with a lot of water in order to rid it of soluble (chromium-free) by-products which would otherwise impair the catalytic properties (Chim. Ind. (Milano) 64 (1982) page 137, Table 2). The required washes mean considerable expenditure in time and material. This process leads to a product having a high chromium content.

It is a further disadvantage that articles molded from hydrated chromium oxides prepared in this way are of low mechanical stability (East German Pat. No. 117,444). A previous attempt at solving this problem took the form of applying suitable chromium compounds to mechanically stable supports. In this method, the hydrated chromium oxide can be produced from chromium by impregnating the support with a chromium(VI) compound and a subsequent reduction (German Offenlegungsschrift No. 1,443,197). Similarly, a support can be impregnated with a chromium(III) salt solution and then the chromium hydroxide be precipitated by means of alkali (German Auslegeschrift No. 1,210,783).

Hydrated oxides applied to a support can be converted into a catalytically active form by subjecting them to a thermal treatment and/or fluorination with hydrogen fluoride. Examples of suitable support materials for hydrated chromium oxide are alumina, aluminum fluoride, magnesium fluoride (German Offenlegungsschrift No. 1,443,382) and active charcoal.

If supported catalysts are prepared on the basis of chromium (VI) compounds (which are then reduced), a further disadvantage, in addition to that of the toxicity of the starting material, is the comparatively high expense of removing soluble by-products. Finally, owing to their low chromium content these supported catalysts are less active than pure hydrated chromium oxides.

For instance, a catalyst comprising activated hydrated chromium oxide on active charcoal with a 14% by weight chromium content produces under certain conditions only a yield of 1% pentafluorochloroethane in the reaction of hexachloroethane with hydrogen fluoride (Example 10 of East German Pat. No. 119,033). An unsupported catalyst consisting of hydrated chromium oxide, however, produces under similar conditions a pentafluoroethane yield of 68% for the same reaction (Example 4 of East German Pat. No. 117,963).

It is known to add binders in order to increase the mechanical strength of catalyst moldings. For instance, it is possible to improve the mechanical strength by coprecipitating a chromium(III) salt and a magnesium salt under alkaline conditions (Japanese Preliminary Published Application No. 74-43,922). The catalyst used contains for example 2 to 30% by weight of magnesium. Chromium is present as hydrated oxide.

The mechanical strength of the catalyst can be increased, according to U.S. Pat. No. 3,978,145, by adding 15% of magnesium oxychloride binder (Sorel cement) to hexagonal CrOOH.

The result of preparing hydrated chromium oxide by reducing chromium trioxide in the presence of magnesium fluoride is catalysts having improved properties. The magnesium fluoride content is at most 50% (U.S. Pat. No. 3,992,325).

It is thus the object of the invention to find catalysts for carrying out fluorination and/or dismutation reactions on halogenated hydrocarbons with hydrogen fluoride in the gas phase as well as a process for preparing the catalysts which avoids the use of toxic chromium(VI) compounds and the need for expensive washes. The catalyst prepared by the process according to the invention shall be mechanically very stable without additional measures and be highly active.

This object is achieved by finding a chromium-containing catalyst for fluorination and/or dismutation reactions on halogenated hydrocarbons with hydrogen fluoride in the gas phase which contains at least 55% by weight of magnesium fluoride and 0.5 to 29% by weight of chromium, the atomic ratio of magnesium to chromium being between 1.5 and 50. In this catalyst the chromium is present not as chromium trifluoride.

The process for preparing the novel chromium-and magnesium-containing catalyst for fluorination reactions involves as the key step the precipitation of chromium(III) hydroxide and comprises reacting 1 mole of a water-soluble chromium(III) salt with at least 1.5 moles of magnesium hydroxide or magnesium oxide in the presence of water, converting the reaction mixture—if necessary by evaporation—into a paste which contains chromium hydroxide and a magnesium salt, drying the paste and treating it with hydrogen fluoride at temperatures of 20° to 500° C. Depending on the magnesium excess used the paste can further contain MgO or Mg(OH)$_2$.

The chromium(III) compounds used can be anhydrous or advantageously the hydrated salts of trivalent chromium which are readily accessible and commercially available. Examples of compounds which can be used are chromium sulfate, and chromium fluoride, but chromium(III) chloride and chromium(III) nitrate are preferable.

The starting magnesium oxide must not have been calcined, but must still be capable of reacting with weakly acid compounds. Since the catalyst is prepared without intermediate washing, the molar ratio of magnesium to chromium for the starting components equals that of the finished catalyst. It is advantageous to start the reaction with an atomic ratio of chromium to magnesium from 0.001 to 0.66, preferably from 0.04 to 0.5. Surprisingly, very active catalysts are obtained even if the chromium content is as low as 1% by weight. Chromium contents of 1 to 20% are preferable. In most cases, the reaction is started with 12 to 24 moles of magnesium oxide or magnesium hydroxide per mole of chromium(III) salt, which corresponds to atomic ratios of chromium to magnesium from 0.04 to 0.08 in the finished catalyst.

The amount of water used in the reaction is not critical; however, sufficient water must be present for the mass to be at least workable with a kneader. The higher the starting amount of water, the more water has to be evaporated at the end.

One way of preparing the catalysts according to the invention is to add an aqueous solution of the chromium compound to dry magnesium oxide (or hydroxide) and to knead the resulting reaction mixture into a paste.

It is also possible to add water to the magnesium oxide, form a paste, add the chromium compound in the dry state, and to knead the reaction mixture. The kneading is advantageously effected with machines which are customary in process technology for mixing pastelike materials (for example vertical kneaders or Duplex kneaders).

An intermediate product of the preparation of catalysts according to the invention is a paste which is dried without prior washing. It is immediately suitable for preparing moldings. It is an advantage that the moldings can be prepared using conventional processing measures, for example pelletization, extrusion or granulation. The catalysts are suitable for use in fixed-bed, moving-bed and fluidized-bed reactors.

The molding is followed by drying the catalyst moldings, which leads to mechanically very stable catalyst bodies. The drying can take place not only at room temperature but also at elevated temperatures. The drying temperature is advantageously between 50° and 150° C., preferably 70° C. and 120° C., in order to shorten the drying time. The drying can take place not only under atmospheric pressure but also under reduced pressure.

The drying should not be done at temperatures above 400° C., since otherwise the chromium oxide looses its reactivity towards hydrogen fluoride, chromium oxyfluoride not being formed any longer (column 4 of U.S. Pat. No. 3,258,500).

The treatment with hydrogen fluoride is advantageously carried out at a temperature at which the volatile reaction products (H$_2$O and HF) do not condense. Temperatures of 100 to 400° C., preferably 120 to 220° C., are advantageous. The starting amount of hydrogen fluoride is not critical. Effective catalysts are obtained even if the catalyst material is treated with as little as 2 moles of hydrogen fluoride per mole of starting metal compound (chromium salt and magnesium oxide). Higher levels of hydrogen fluoride are also possible; their use is only limited by economic considerations. The fluorination time can be varied within wide limits; 0.5 to 10 hours are preferred. In order to speed up the removal of the resulting water and to avoid undesirable temperature peaks, the HF can be diluted with an inert gas, for example N$_2$ or air.

The treatment with hydrogen fluoride for activating the catalyst material is advantageously carried out in the same apparatus in which the catalyst will later be used for fluorinating halogenated hydrocarbons.

The catalysts prepared using the process according to the invention can be immediately used for fluorination and/or dismutation reactions on halogenoalkanes. There is no need to activate the catalyst by calcining it.

It is also possible to prepare catalysts of virtually the same gross composition by mixing pulverulent hydrated chromium oxide with pulverulent magnesium fluoride and treating the mixture with hydrogen fluoride. This mixture, however, has markedly poorer catalytic and mechanical properties than the catalyst prepared according to the invention.

The following Examples illustrate the invention in more detail:

EXAMPLE 1

1 part by weight of CrCl$_3$.6H$_2$O is dissolved in 10 parts by weight of water. This solution is added to a mixture of 3.85 parts by weight of magnesium oxide and 1.23 parts of weight of graphite, and the resulting pastelike mixture is intimately kneaded.

The pastelike reaction product is then granulated into cuboid moldings (0.5 cm edge length) which are dried at 100° C. for 16 hours.

0.33 liter (bulk volume) of the dried catalyst bodies (=200 g) is treated at 200° C. with 5 moles of hydrogen fluoride in a nickel or VA stainless steel tube which has an internal diameter of 5 cm and is 100 cm long. The treatment with hydrogen fluoride lasts about 3 hours. The hydrogen fluoride used is diluted with N$_2$. The fluorination catalyst obtained has a chromium content of 1.6% by weight.

EXAMPLE 2

1 part by weight of Cr(NO$_3$)$_3$.9H$_2$O is dissolved in 5 parts by weight of water. This solution is added to a mixture of 2.5 parts by weight of magnesium oxide and 1.2 parts by weight of graphite. The onward processing and hydrogen fluoride treatment are carried out as described in Example 1. The illustrative fluorination catalyst has a chromium content of 2.3% by weight.

EXAMPLE 3

1 part by weight of Cr(NO$_3$)$_3$9H$_2$O is dissolved in 2.78 parts by weight of water. This solution is added to a mixture of 1.39 parts by weight of magnesium oxide and 1 part by weight of graphite. The onward processing and hydrogen fluoride treatment are carried out as described in Example 1. The illustrative fluorination catalyst contains 2.7% by weight of chromium.

EXAMPLE 4

1 part by weight of $Cr(NO_3)_3.9H_2O$ is dissolved in 1.39 parts by weight of water. This solution is added to a mixture of 0.69 parts by weight of magnesium oxide and 0.68 parts by weight of graphite. The onward processing and hydrogen fluoride treatment are carried out as described in Example 1. The illustrative fluorination catalyst contains 4.3% by weight of chromium.

EXAMPLE 5

1 part by weight of $CrF_3.4H_2O$, 1.67 parts by weight of MgO and 0.93 parts by weight of graphite are mixed in the dry state, the mixture is turned into a paste with 5.47 parts by weight of water and the paste is kneaded. The onward processing and hydrogen fluoride treatment are carried out as described in Example 1. The illustrative catalyst contains 7.3% by weight of chromium.

The following Examples demonstrate the effectiveness of the catalysts according to the invention in fluorination and dismutation reactions.

EXAMPLE 6

570 g of carbon tetrachloride and 120 g of hydrogen fluoride are passed in the gaseous state for 3 hours over 330 cm³ of the fluorination catalyst prepared in Example 1 and held at a temperature of 200° C. by means of an electrical resistor.

The reactor comprises the same tube as already used for the hydrogen fluoride treatment in the preparation of the catalyst.

The gaseous reaction products leaving the reactor are passed to a water-filled wash apparatus in which the acid mixtures to be analyzed are trapped.

The hydrogen fluoride conversion values in the Examples in question are determined by titrating the wash fluid. The values obtained are potentiometrically checked using a fluoride-specific electrode. The gaseous water-insoluble reaction products are analyzed by gas chromatography.

The HF conversion for the fluorination catalyst prepared in Example 1 is 99.5%.

The leaving gas from the reaction has the following composition:
$CCl_4$:11.8% (by volume)
$CFCl_3$:21.6%
$CF_2Cl_2$:65.1%
$CF_3Cl$: 1.5%

EXAMPLE 7

The fluorination catalyst prepared in Example 2 is used for fluorinating carbon tetrachloride with hydrogen fluoride in the same experimental set-up as in Example 6. The reactor temperature is 140° C. The HF conversion is 99.7%.

The leaving gas from the reaction has the following composition:
$CCl_4$:9.3%
$CFCl_3$:25.1%
$CF_2Cl_2$:61.6%
$CF_3Cl$: 3.8%

EXAMPLE 8

The fluorination catalyst prepared in Example 3 is used for fluorinating carbon tetrachloride with hydrogen fluoride in the same experimental set-up as in Example 6. The reactor temperature is 180° C. The HF conversion is 99.6%.

The leaving gas from the reaction has the following composition:
$CCl_4$:11.1%
$CFCl_3$:19.2%
$CF_2Cl_2$:54.8%
$CF_3Cl$: 14.3%

EXAMPLE 9

The fluorination catalyst prepared in Example 4 is used for fluorinating carbon tetrachloride with hydrogen fluoride in the same experimental set-up as in Example 6. The reactor temperature is 140° C. The HF conversion is 99.8%.

The leaving gas from the reaction has the following composition:
$CCl_4$:8.7%
$CFCl_3$:15.7%
$CF_2Cl_2$:70.6%
$CF_3Cl$: 4.6%

EXAMPLE 10

The fluorination catalyst prepared in Example 5 is used for fluorinating carbon tetrachloride with hydrogen fluoride in the same experimental set-up as in Example 6. The reactor temperature is 200° C. The HF conversion is 99.5%

The leaving gas from the reaction has the following composition:
$CCl_4$:8.9%
$CFCl_3$:13.2%
$CF_2Cl_2$:75.4%
$CF_3Cl$: 3.4%

EXAMPLE 11

In the same experimental apparatus as in Example 6, 450 g of chloroform and 120 g of hydrogen fluoride are passed in the gaseous state for 3 hours over 0.33 liter (bulk volume) of the fluorination catalyst prepared in Example 2 and maintained at a temperature of 207° C. The HF conversion is 98.9%.

The leaving gas from the reaction has the following composition:
$CHCl_3$:22.3%
$CHFCl_2$:4.7%
$CHF_2Cl$: 5.6%
$CHF_3$:67.4%

EXAMPLE 12

In the same experimental apparatus as in Example 6, 60 g of tetrafluorodichloroethane are passed for one hour over 0.33 liter (bulk volume) of the catalyst prepared as in Example 2 and maintained at a temperature of 300° C. The product gas leaving the reactor has the following composition:
$C_2F_2Cl_4$:5.8%
$C_3F_3Cl_3$:14.8%
$C_2F_4Cl_2$:59.4%
$C_2F_5Cl$: 20.1%

EXAMPLE 13

The catalyst prepared in Example 4 is used in an experimental apparatus as in Example 12 for dismutating tetrafluorodichloroethane at 300° C. The product gas leaving the reactor has the following compositions:
$C_2F_2Cl_4$:5.5%

$C_2F_2Cl_3$: 16.5%
$C_2F_4Cl_2$: 50.5%
$C_2F_5Cl$: 27.5%

What is claimed is:

1. A process for preparing a chromium-and magnesium-containing catalyst for fluorination reactions by precipitating chromium (III) hydroxide, which comprises reacting 1 mole of a water-soluble chromium (III) salt with at least 1.5 moles of magnesium hydroxide or magnesium oxide in the presence of water, converting the reaction mixture into a paste which contains chromium hydroxide and a magnesium salt, drying the paste and treating it at temperatures of 20° to 500° C. with at least two moles of hydrogen fluoride per mole of metal compound, chromium (III) salt plus magnesium hydroxide or oxide, in the starting material.

2. The process as claimed in claim 1, wherein the paste is molded before it is dried.

3. The process as claimed in claim 1, wherein 12 to 24 moles of magnesium oxide or magnesium hydroxide are used per mole of chromium(III) salt.

4. The process as claimed in claim 1, wherein chromium(III) chloride or nitrate is used.

5. The process as claimed in claim 1, wherein the paste is formed by evaporation of said reaction mixture.

6. A chromium- and magnesium-containing catalyst made according to claim 1, which comprises at least 55% by weight of magnesium fluoride and 0.5 to 29% by weight of chromium, present in the form of a chromium compound, the atomic ratio of magnesium to chromium being between 1.5 and 50.

* * * * *